United States Patent [19]
Takemura et al.

[11] Patent Number: 5,374,989
[45] Date of Patent: Dec. 20, 1994

[54] APPARATUS FOR IDENTIFYING AN OBJECT UTILIZING A TRACKING MEANS AND AN IDENTIFICATION BEAM

[75] Inventors: Yasuhiro Takemura, Urayasu; Toshiharu Takesue, Chiba, both of Japan

[73] Assignee: Sumitomo Cement Co. Ltd., Japan

[21] Appl. No.: 142,988

[22] Filed: Oct. 29, 1993

[30] Foreign Application Priority Data

Oct. 29, 1992 [JP] Japan .................................. 4-291565

[51] Int. Cl.$^5$ ............................................ G01N 15/02
[52] U.S. Cl. .................................. 356/336; 356/400; 356/343; 250/556
[58] Field of Search .................. 356/400, 336, 343; 250/203.2, 556

[56] References Cited

U.S. PATENT DOCUMENTS 5,315,115 5/1994 Gerber et al. ..................... 356/336

Primary Examiner—F. L. Evans
Assistant Examiner—Robert Kim
Attorney, Agent, or Firm—Hoffman, Wasson & Gitler

[57] ABSTRACT

A method and apparatus for identifying an object having non-specific outer boundaries, such as a leukocyte, includes a device for tracking, in two dimensions, the position of the object to be identified. An identification device for identifying the object tracked by the device includes a coherent light beam emissions source, a lens assembly to direct the coherent light beam from the source to the object to be identified, a detection device for detecting the light beam which is transmitted through the object, the detection device provided with a plurality of circular or semicircular coaxial sections, the center of which is at the axis of the coherent light beam in the plane on which Fraunhofer's diffraction patterns are formed. Finally, an identification apparatus is provided which uses the output of the detection device to provide various characteristic parameters which are utilized to identify the object.

16 Claims, 8 Drawing Sheets

FIG. 2
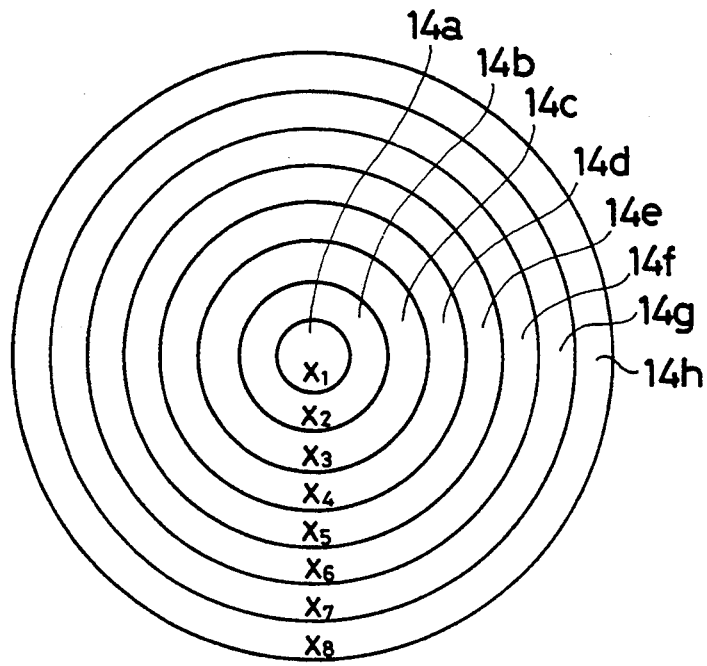
$X = \{X_1, X_2, X_3, X_4, X_5, X_6, X_7, X_8\}$
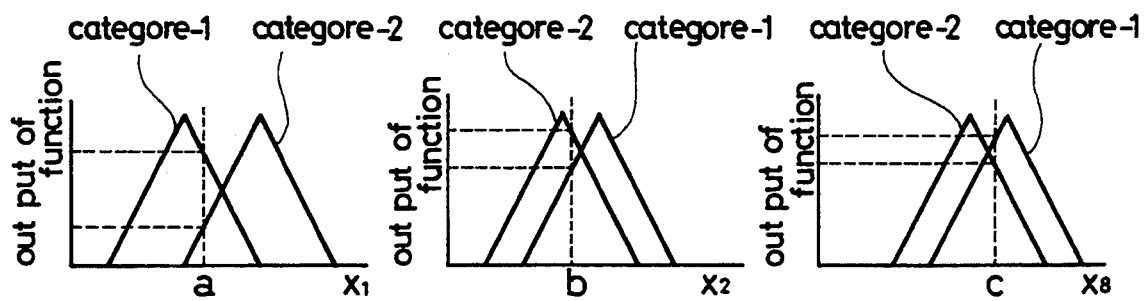
FIG. 3A    FIG. 3B    FIG. 3C

APPARATUS FOR IDENTIFYING AN OBJECT UTILIZING A TRACKING MEANS AND AN IDENTIFICATION BEAM

BACKGROUND OF THE INVENTION

1. Field of the Invention

The present invention relates to an apparatus for identifying an object having non-specific outer boundaries, such as a leukocyte in blood, a leukemia, a microorganism in water, the ground, or an animal body, as well as a protein deposited from a solution, as utilized in the medical field.

2. Description of the Prior Art

There has been proposed as prior art an apparatus for identification of an object having a non-specific outer boundary, such as a leukocyte. In this apparatus, a leukocyte can be tracked by utilizing the difference in chromatic dispersion from a rhodocyte in blood containing a leukocyte and a rhodocyte in microphotometry. The microphotometric image is analyzed by using digital image processing technology, in view of the measured area of a nucleus and circumference of the nucleus, and areas of cytoplasm and cytoplasmic granules, and further, data on color of the nucleus and cytoplasmic granules as characteristic parameters. The leukocyte can be identified logically in view of such characteristic parameters.

This type of prior art apparatus utilizes digital image processing theory which provides the characteristic parameters of the image. Since the amount of data needed to be processed is large, employing a relatively inexpensive computer will result in a significantly slow processing rate. Consequently, a relatively expensive computer exhibiting high performance must be used to provide a sufficiently high rate of processing.

Parameters with regard to configurations of a cell nucleus, cytoplasm and cytoplasmic granules are vague so that the particular identification method depends largely on the condition of the images to be analyzed, resulting in a large number of incorrect analyses.

Furthermore, in situations where one correctly identifies an object, images having significantly low contrast and structure are obtained so that the digital image processing, in many instances, does not afford characteristics that the human eye can distinguish.

SUMMARY OF THE INVENTION

Accordingly, it is an object of the present invention to provide a fairly inexpensive apparatus to correctly identify an object, using a semiconductor laser and liquid crystal panel to detect characteristic parameters, thereby decreasing the amount of data to be processed with high speed processing.

It is another object of the present invention to provide a stable identification system without any detrimental influence on digitalization image processing, a process in which identification is not affected by staining conditions, such as in the shape and contrast of the object.

BRIEF DESCRIPTION OF THE DRAWINGS

The objects and features of the present invention will become more apparent from the consideration of the following detailed description taken in conjunction with the accompanying drawings in which:

FIG. 2 shows schematically the configuration of a ring detector to be used in accordance with the present invention;

FIG. 3 shows schematic graphs illustrating the relation of each parameter to functions to be used in the apparatus, and a procedure to be used in accordance with the present invention;

DETAILED DESCRIPTION OF PREFERRED EMBODIMENTS

Figure 1:
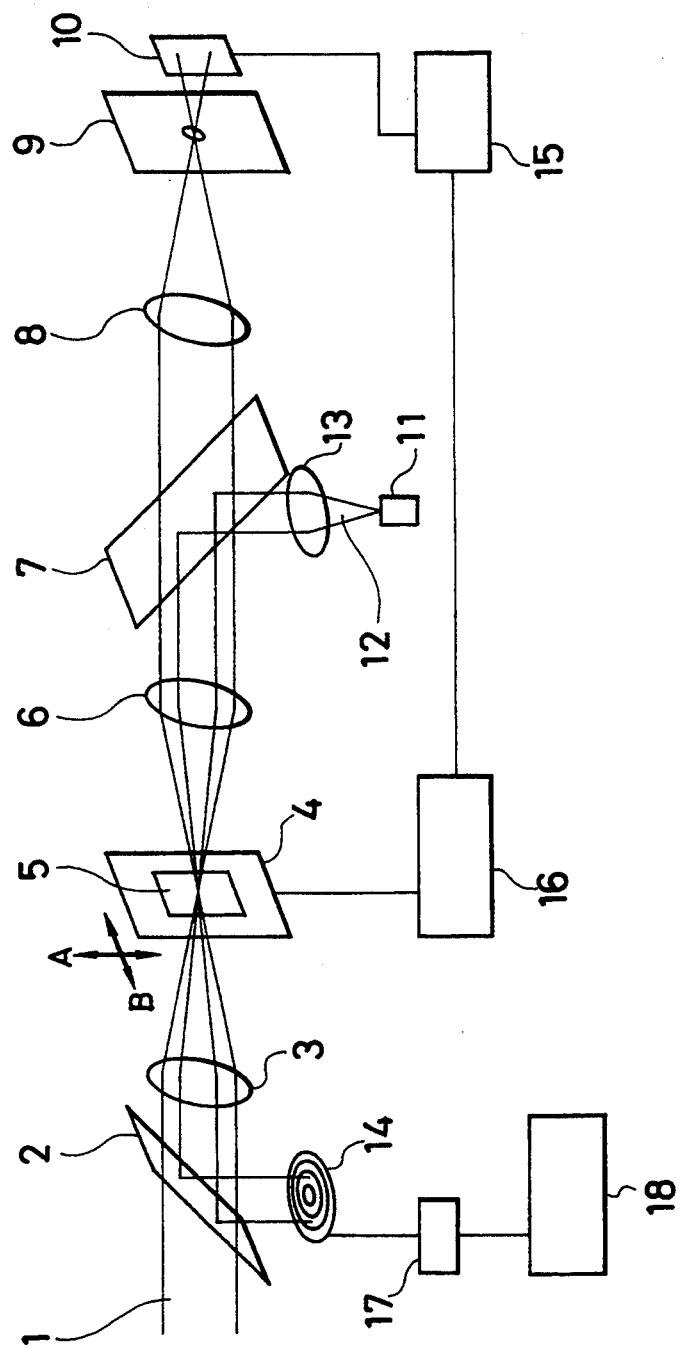
FIG. 1 shows schematically an optical configuration of one example of an apparatus for identification of an object in accordance with the present invention.

In accordance with the present invention, an object or a species of the object can be identified by an apparatus comprising a tracking device for tracking a position of the object to be identified and an identification device for identifying the object tracked by the tracking device. The identifying device comprises at least (a) a source for emitting a coherent light beam; (b) a lens assembly to direct the coherent light beam from the source to the object and the region neighboring the object; (c) a detecting device for detecting the light beam having transmitted through the object, provided with a plurality of circular or semicircular coaxial sections, the center of which is at the axis of the coherent light beam, in a plane on which Fraunhofer's diffraction patterns are formed with regard to a plane containing the object; and (d) an identification apparatus for identifying the object by use of an output of the detecting device corresponding to each of the sections of the detecting device, on the basis of the characteristic parameters of the object, as obtained.

Preferably, a lens assembly can be used also as an objective lens for enlarging or tracking the object. Further, preferably, the coherent beam is focused on the object by the objective lens, and the detecting region is a certain distance apart from the object.

In accordance with the present invention, the device for identifying the object comprises at least an optical device for forming an enlarged image or a reduced image of the object, an image sensor for detecting an image of the object, a display for coherently displaying the image of the object, as obtained by the image sensor, and a source for emitting a coherent beam. Also included is a lens assembly for directing the coherent beam to the image of the object and its displayed neighborhood, and a detecting device for detecting the coherent beam, having a plurality of detecting sections with circular or semicircular shape, which are coaxial to the optical axis of the coherent beam, thereby identifying the object on the basis of characteristic parameters which are calculated from the output of the detecting device corresponding to each of the sections.

Preferably, a device for transforming, in real-time, the contrast thereof and reversing the density of the images may be provided between the image sensor and the display. In this instance, identification is preferably effected by a neural network device to which input data are the characteristic parameters, and output data reflect the identification of each of the categories.

The device for tracking the object comprises at least a device for moving the object in two dimensions, a second imaging device for obtaining the image of the object; a filter having transmissivity relatively higher than the specific wavelength of light and relatively lower than another wavelength of light; and a linear sensor provided at the imaging point of the second imaging device of the object. The linear sensor comprises a plurality of photoelements arranged linearly in one of the directions in which the object is moved by the moving device, and the transmissivity or reflectance thereof is distributed so that the image of the object has the proper amount of light with regard to the specific wavelength range relative to the background thereof. Furthermore, the second imaging device has two or more branch passages in which each passage has the same focused image, and each of the wavelength filters has higher transmissivity with regard to different wavelength ranges of each of the passages. The linear sensor is provided with each of the passages, and arranged in line in the same direction as one of the moving directions of the moving device, so as to process each of the outputs from each of the line sensors, thereby enabling a determination as to whether the object is present or not, and the position of the object.

The tracking device comprises at least a tube in which a solution containing the object as a solute passes, the width of which is as large as the maximum size of the object to be identified, and comprising a material in which an optical beam cannot be highly dispersed.

Furthermore, in the identification device, the characteristic parameters are input data, in which the average amount of the parameters with regard to a plurality of the object is estimated, and then, the difference between the average and each of the parameters with regard to each of the categories is calculated as a variable. In one case, where this difference is positive, a monotonous non-decreasing function is formed. However, if the difference is negative, a monotonous non-increasing function is formed. The identification is exerted by using a minimum value when the function of the output with regard to the input parameters for each of the categories is in the latter case, or using a maximum value when the function is in the former case.

The device for identifying the object can preferably determine an average slope of the function of the parameters, on the basis of a variance of the parameters with regard to a plurality of the sample objects. Preferably, a neural network to which an output of the function with regard to each of the categories is input data to be processed, and an output to be used for identification is an identification value with regard to each of the categories is employed. Furthermore, the identification is exerted on the basis of a combination of minimum values or maximum values of the output of the function with regard to the characteristic parameters, and the identification output of the neural network device to which the input data is an output value of the function with regard to each of the functions of the categories.

In the composition of the apparatus for identifying an object, a coherent light beam emitted from a coherent source passes through a lens assembly and strikes an object to be identified. At this time, the coherent beam is modified spatially by the object to be identified, into a complex amplitude distribution. The beam is then transmitted or reflected and emitted from the object. The emitted coherent beam will form a Fraunhofer's diffraction image of the irradiated pattern including substantially the input object at a position sufficiently far from the object.

The position sufficiently far from the object can be determined by the size of the object, or the diameter of the beam which is to be incident on the object. When the diameter of the beam is about 10 micrometers, the distance of the position from the object would be several millimeters. When the diameter is about several millimeters, the distance would be several meters. In this case, a converging lens should be used to provide the position at which Fraunhofer's diffraction image is formed in an approximate position of the focus plane. A plane at which Fraunhofer's diffraction image can be detected is called an "optical Fourier transformation plane". On this Fourier transform plane, the intensity distribution of the beam forms an intensity spectrum with regard to a complex amplitude distribution of the beam, immediately after the beam is emitted from the object. The beam is detected by a plurality of detectors, which comprise a plurality of detecting circular regions coaxial to the axis of the beam.

Each of the outputs of each of the regions can be obtained on the basis of the amount of light detected by each of the regions. Each of the outputs forms an output responsive to each component of spatial frequency corresponding to the structure of the object. Because the necessary time to yield these outputs is only the sum of the transmission time of the beam, and the response time of a detector in the output amplifier, it can be rapidly processed with significantly high speed.

The object may be reviewed and tracked by optically enlarging the object by use of a microscope. In this case, when the objective lens is a Fourier transform lens, the optical system can be simplified.

When a coherent source is provided at the position opposite to the object with regard to the objective lens, the coherent beam passing through an objective lens is focused on the object. In this instance, an intensity spectrum pattern of the complex amplitude distribution of the beam on the object can be detected at the position sufficiently far from the object, by the beam passing through the object. In this case, the characteristic parameters of the object can be obtained by this significantly simple system.

The image formed by the optical system is transformed by the apparatus of the present invention into electric signals from the image sensor, and displayed on a display.

The coherent beam emitted from the source is transmitted through a lens assembly and strikes the object. The coherent beam then transforms the complex amplitude distribution of the image of the object and its background as displayed on the display, and transmits the image, or the reflection of the image, from the display. The coherent beam from the display can form a Fraunhofer diffraction image of the irradiated pattern, including the object at a position far enough from the display. This position can be determined by the size of the image of the object formed on the display, i.e. the diameter of the beam including the image of the object. When the diameter is about, 10 micrometers, the distance from the object would be several millimeters. Further, when the diameter is more than several millimeters, the distance would be more than several meters, and then, the position at which Fraunhofer's diffraction image is substantially formed can become a determinable distance by using the lens to focus the beam.

The plane at which the Fraunhofer diffraction image can be formed, i.e. an optical Fourier transform plane, has an intensity distribution of the beam which becomes an intensity spectrum distribution with regard to the complex amplitude distribution of the beam just after being emitted from the display. A plurality of circular detecting regions, which are coaxial to the axis of the beam, and each of the detecting regions give, respectively, the output on the basis of the amount of light received by each of the detecting regions. Therefore, each of the outputs represents each of the outputs corresponding to spatial frequency components of the structure of the object. The necessary time to yield such outputs is only a combination of the time to detect and display the image of the object, and the time to transmit the beam, the response time of the detectors and the amplifier for the outputs.

An image signal produced by the image sensor can be significantly improved by certain processing. A density conversion can elongate or expand an important portion of the image which is significant in density. When the object to be identified has higher density than that of the background, a reverse concentration processing should be exerted, so as to improve significantly the ratio of the signals with regard to the object, as included in a Fourier transform image, formed on an optical Fourier transform plane, to the other signals.

In the device for tracking the object, the object is two-dimensionally scanned by moving the object in two dimensions to search for the position of the object in the sample. At this time, the object is detected by a second optical system to form the image of the object on a linear sensor positioned in the direction of scanning of the moving device. The beam passes through a specific filter having higher or lower transmissivity with regard to a wavelength range specific to the object. When the image of the object is at a specific position on the linear sensor, the output of the linear sensor is changed in comparison with the instance when no object is detected. Therefore, the measurement of change of the amount of light on the linear sensor at a specific position will be determined by whether the object is present or not present within the linear sensor. At this time, the position of the object can be determined.

Furthermore, when the light distribution of the images of the object and its background is similar with regard to a specific wavelength range, and it is significantly different with regard to a second specific wavelength range, both light amounts with regard to the two specific wavelength ranges should be primarily combined to obtain an output only with regard to the object, with good definition. A second light passage can be divided from a main light passage, and the image of the object can be formed in each of the divided passages, and a wavelength filter can be provided in each of the passages with regard to each of the specific wavelength ranges. The formed image can be detected by each of the detectors of the linear sensor provided in each of the passages. At this point, an output from the linear sensors can be processed, to provide the output of the image rather than that of the background, thereby determining the position of the object.

The object having a non-specific shape has primarily specific characteristics in spatial frequency distribution of its structure. Consequently, the output from the detecting region can be used as characteristic parameters. This is especially true when the detecting region is finely divided, the number of the parameters becomes larger, and then, it is preferable to select only the parameters which contribute significantly to the identification of the object.

When the object is directly exposed to the beam, the concentration distribution can be easily Fourier transformed as a phase distribution, even when the contrast of the image is lower. This resulting distribution can surely represent the intensity spectrum on the detecting region.

These parameters can be more easily and effectively identified by using a learning type identifying device utilizing a neural network. In the neural network, the learning can increase the weight of the identification standard to the parameters having a higher contribution with regard to each of the categories. Conversely, the learning can decrease the weight to the parameters having lower contribution with regard to each of the categories. Further, when a plurality of the categories having similar characteristics are provided, the portions having a difference in characteristics can be emphasized for identification. Therefore, when there are many characteristic parameters, they can identify the object which cannot be identified visually by humans. The standard for identification can be produced even when it is impossible to visually identify the object.

Furthermore, with regard to these characteristic parameters, a fuzzy set can be produced with regard to each of the parameters for each of the identification categories on the basis of the average of the parameters and variance of the parameters of the samples. Where the fuzzy set is a convex-shaped fuzzy set, each of the parameters of the object has each membership value with regard to the fuzzy set. These membership values will be higher the closer each of the parameters is to its average. A category in which the minimum of the membership values is highest should be a result of the identification.

Further, these membership values are provided as inputs into the neural network device, and then, the neural network device learns the extent of contribution to the identification of each of the inputs, each of the weights of the parameters being evaluated on the extent of contribution. Therefore, even when the dispersion of the characteristic parameters is higher, and when the parameters are similar between the categories, the difference between one category and another category can be emphasized so as to enable identifying the object.

In the case where it is inconvenient to identify the object having much different parameters than that of a learning sample regarding the category to which an object belongs, the minimum of the membership values is significantly small, when the input data is much different from the sample data for preparation of the fuzzy set. Therefore, some conditions should be applied to such value, so as to minimize mistaken identification of the object which has not yet been learned and has much different membership values from that of the learned object.

The present invention is further illustrated by the following examples to show an apparatus for identifying an object, but should not be interpreted for the limitation of the invention.

EXAMPLE 1

FIG. 1 shows schematically one preferred embodiment of the inventive apparatus of identification.

An object to be identified is enclosed within an enclosure, set on a sample table 4, and stained so as to distinguish the object to be identified from the other substances by the difference in transmissivity at a specific wavelength range. An irradiation beam 1 for tracking the object to be identified is focused by a first lens 3 onto an object 5 mounted on the sample table 4. The irradiation beam 1, transmitting through the object 5, passes through a second lens 6, a beam splitter 7 and a third lens 8 and reaches a mask 9. The mask 9 has an aperture which is the same size as that of the object to be identified. The aperture has dispersion properties relating to a specific wavelength range.

The sample table 4 can be moved in the directions A or B as shown by the arrows in FIG. 1, by a control circuit 16 to move the table 4 in a controlled manner. Only when the object 5 to be identified is projected onto the aperture of the mask 9, a signal showing such event is sent to a detecting circuit 15, therefore positively indicating that the object to be identified is present at the specific position. The irradiation beam 1, the sample table 4, the table control device 16 to move the table 4 in a controlled manner, the mask 9, a photodetector 10 and the detecting circuit 15 comprise the device for tracking the object to the identified. It is to be noted that such composition of the apparatus is but one of several devices for tracking the object and the position of the object. Further embodiments thereof will be subsequently illustrated.

As described above, the object to be identified can be tracked. Subsequently, a coherent light beam 12 emitted from a semiconductor laser 11 is made into a substantially parallel beam by a fourth lens 13. This beam is reflected by the beam splitter 7, and passes through the second lens 6, is focused and made incident on the object 5. The table is then moved and controlled so that the incident coherent beam 12 can radiate accurately on the object to be tracked. In a simplified explanation, when the assembly for tracking the position of the object and the optical assembly for the coherent beam 12 are combined, the movement of the table is stopped at the time when the object is detected by the detecting circuit 15, and the coherent beam 12 is made accurately incident onto the object 5.

The diameter of the beam 12 on the object 5 is determined by the ratio of the diameter of the coherent beam 12 through the second lens 6 to the focusing length of the second lens 6 with respect to the wavelength of the coherent beam. When the size of the object is smaller, and the diameter of the beam on the object 5 is made smaller, it is necessary to enlarge the diameter of the beam 12 incident on the second lens 6 with regard to the focal length of the second lens 6.

As described hereinabove, when the size of the object is smaller (in the order of 10 micrometers), the coherent beam 12 passing through the object reaches a Fraunhofer diffraction region, several millimeters to several tens of millimeters apart from the object. Therefore, where a detector is provided at that position, an intensity spectrum of the complex amplitude pattern of the portion of the object which is exposed to the coherent beam 12 is detected. Consequently, the coherent beam 12 passing through the sample 5 is made parallel by the first lens 3, reflected by a beam splitter 2, and received by a ring detector 14. The ring detector 14 can detect the output pattern formed by the beam being reflected by the beam splitter 2, which could be mounted on the sample holder 4, without passing through the first lens 3. However, use of the first lens 3 will have the effect of minimizing the drift of the size of the intensity spectrum pattern in comparison with the dislocation of the position where the optical axis of the ring detectors is located.

The ring detector 14 has a plurality of circular photodiodes arranged transversely and coaxially to the center thereof, which is an optical axis of the coherent beam 12. The number of diodes is preferably between eight and 128. When the number of diodes is excessively small, the information on the characteristic values is insufficient to accurately identify the object. When the number of diodes is excessively large, the rate of processing the identification procedure becomes slow. Further, when the photodiodes having a circular shape are without phase distribution of input patterns, and because it's Fraunhofer's diffraction pattern is in point symmetry, the circular diodes may be semicircular in form.

Current signals based upon the amount of light detected by the ring detectors 14 are transduced into current-voltage by a detecting circuit 17, and amplified to a level high enough to be measured. For example, the ring detectors as shown in FIG. 2 have a plurality of detecting regions. When the assembly of detectors comprises eight sections of ring or circular shape, $14a$, $14b$, ... $14h$, a characteristic vector X (hereinafter a capital"X" indicates a vector) consisting of eight signals (characteristic parameters) $x_1$, $x_2$, $x_3$, $x_4$, $x_5$, $x_6$, $x_7$ and $x_8$ in response to each of the sections is produced via a detecting circuit 17. These characteristic parameters are sent to an identification device 18 in which the object being identified is reviewed or identified as to the particular category to which it belongs. Such identification can be facilitated by reviewing and experimentally determining what regions of the characteristic parameters of the object are present with regard to each of the categories. Then, when all of the parameters do not overlay each other, each of the parameters of the object can be checked by reviewing whether the parameter is present within a certain region which has been previously determined, or on the basis of the combination of such digital image processing theories. Consequently, the identification device 18 can be operated by using a common Von Neuman type computer with the appropriate software, and further, by hardware such as an electronic circuit having the same function.

In this example, a coherent beam is focused on the sample, but when the object is so large that enlargement is not necessary for identification, the coherent beam radiates in mostly parallel form on the object, and transmits through it, and then, is focused by a lens, and an assembly of ring detectors is provided at the focal point of the lens.

EXAMPLE 2

Figure 5:
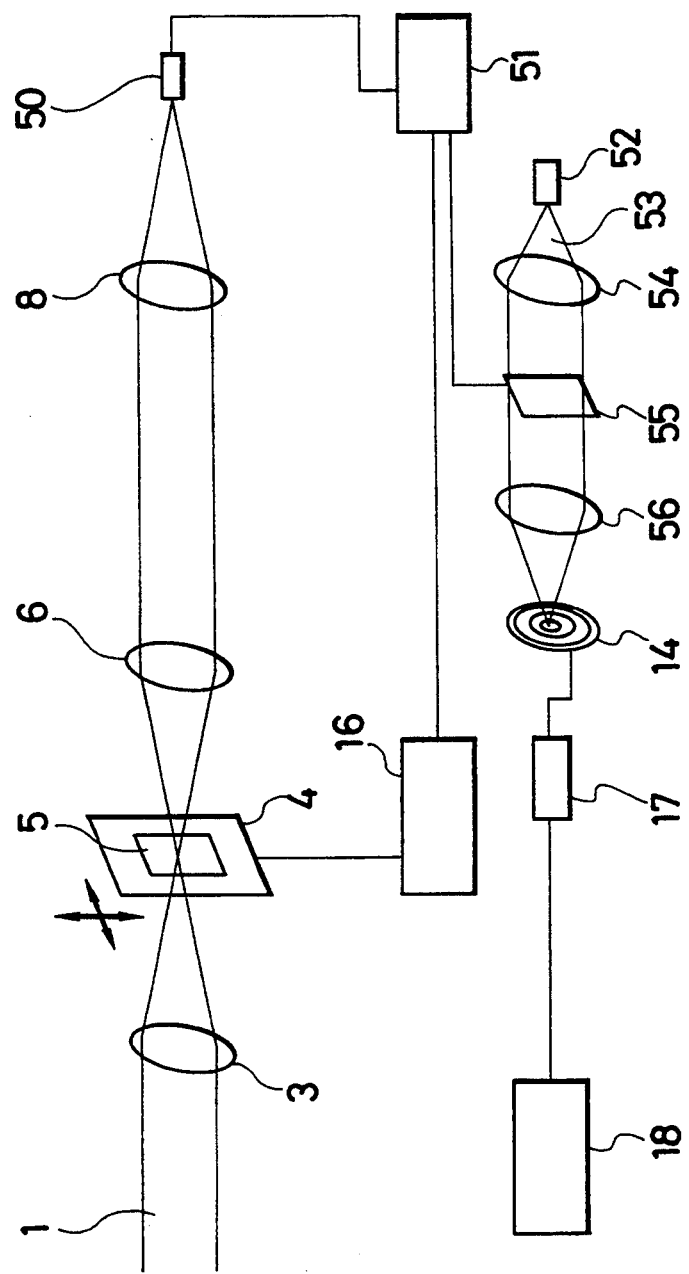
FIG. 5 shows schematically a second embodiment of an apparatus for identification of an object in accordance with the present invention.

FIG. 5 illustrates a second embodiment of the optical apparatus for the identification of an object. As described in Example 1, an object having irregular boundaries is provided, with the material surrounding it, on a sample cell 4. The object 5 to be identified has been chromated or stained to make the transmittance of the object different from that of the background with regard to a specific wavelength. A radiation light beam 1 is focused by the lens 3, and irradiates on a sample mounted on a sample holder. The beam 1 passing through the sample projects through lens 6 and lens 8 and reaches a CCD 50 on which an image of the sample 5 is formed. The lenses 6 and 8 provide a lens assembly to form the image, which, when the image is small, could be a microscope. The CCD 50 is controlled to have sensitivity to a specific wavelength, such that a detecting circuit 51 can detect the object only when the object appears at a specific position in the CCD image plane. The sample holder 4 can De moved in the directions of the arrows shown in FIG. 2 by a holder operating circuit 16. When the image of the object appears at the specific position in the CCD image plane, a signal representing this can be generated by the detecting circuit 51, thereby indicating that the object 5 is present at a specific position in the sample holder. The apparatus for the identification of the object, in accordance with the present invention, comprises the radiation light beam 1, the lens 3, the sample holder 4, the holder moving device 16, the lens 6, the lens 8, the CCD 50 and the detecting circuit 51. Such composition represents an example of the tracking device and the identification device. This embodiment can be modified in accordance with the properties of the object to be identified.

After the object is properly tracked, the image of the object, together with the image of the background can be displayed on a liquid crystal panel 55 through a liquid crystal panel operating circuit provided in the detecting circuit 51. The liquid crystal panel may be a liquid crystal panel which has been used for a liquid crystal TV and a liquid crystal projector. A liquid crystal panel of active matrix type is suitable in view of its contrast and its display rate. Therefore, a coherent beam 53 emitted from a semiconductor laser 52 becomes a parallel beam through a lens 54, and is projected onto the liquid crystal panel 55. The table control device 16 is operated so that the coherent beam 53, to be incident, should irradiate the image of the object tracked. In a simplified case, the detecting signal is generated when the object is present at the central portion of the image panel of CCD 50, and at that time, the movement of the holder is stopped, at which time the coherent beam 53 is incident on the image of the object formed on the liquid crystal panel 55.

When the size of the object is small (about 10 micrometers), the coherent beam emitting from the sample 5 reaches a Fraunhofer diffraction region, several millimeters to several tens of millimeters from the object. Therefore, the coherent beam, to be incident to the sample 5, will reach as a convergent pencil beam to a Fraunhofer diffraction region, at which region a detector is provided so as to detect the intensity spectrum pattern of the complex amplitude pattern resulting from an exposed portion of the liquid crystal panel displaying the image of the object which is exposed to a coherent beam 53. Therefore, the intensity spectrum pattern of the object exposed to the coherent beam 53 emitting from the liquid crystal panel 55 can be detected by the ring detector 14, without use of lens 56. However, at the present time, a liquid crystal panel of matrix type with a resolution high enough to display such a small image of the object is unavailable. An ordinary liquid crystal panel displays a preferably enlarged image of the object having a size of several millimeters, when the object is small. In this case, the coherent beam is preferably a pencil beam becoming incident on the liquid crystal panel 55. The beam emitting from the panel is focused by the lens 56, and the ring detectors 14 are positioned at the focal point of the lens. The focal point corresponds to a Fraunhofer diffraction region with regard to the liquid crystal panel.

The ring detectors 14 are similar to those of Example 1, provided with circular-shaped photodiodes which are arranged transversely and coaxial to the optical axis of the coherent beam 53. The number of the photodiodes is preferably 8 to 128. When the number is too small, the characteristic information to accurately identify the object will be insufficient. When the number is too large, the rate of processing for identification becomes slow. The circular detectors may be semicircular in form because the Fraunhofer diffraction pattern is in point symmetry when the input pattern is displayed only by intensity distribution.

The processing of the signals generated on the basis of the amount of light detected by the ring detectors is similar to that of Example 1, and the description thereof is omitted.

The image of the object may have lower contrast, or a high density of the portions containing the characteristics rather than the surrounding background there. In this situation, an analog to digital (AD) converter of the input image signal, and a look-up table to convert in density the AD converted image digitalized data, and a density converting means comprising a DA transducer for transducing from the density-converted data into analog signals are effectively provided between the CCD 50 and the detecting circuit 51. In this case, the look-up table should be operated so as to expand the density distribution of the portion showing the characteristics of the object, and further to invert the image density when the image of the object has a higher density than the background thereof.

EXAMPLE 3

In this Example, the device for tracking the position of an object will be described in detail. For example a sample having blood coating may be scanned by using Mayglunwaid-Gimmuza staining for identification of leukocytes. This kind of staining imparts green color, i.e. lower transmissivity of the leukocyte nuclei or granules with regard to the wavelength range approximate to 550 nm. A filter having higher transmissivity at this wavelength range and lower transmissivity at a second wavelength range is used to emphasize the leukocyte from the background and the erythrocytes, and further enabling the tracking of the nuclei of the leukocyte. This apparatus is described with reference to FIG. 6.

Figure 6:
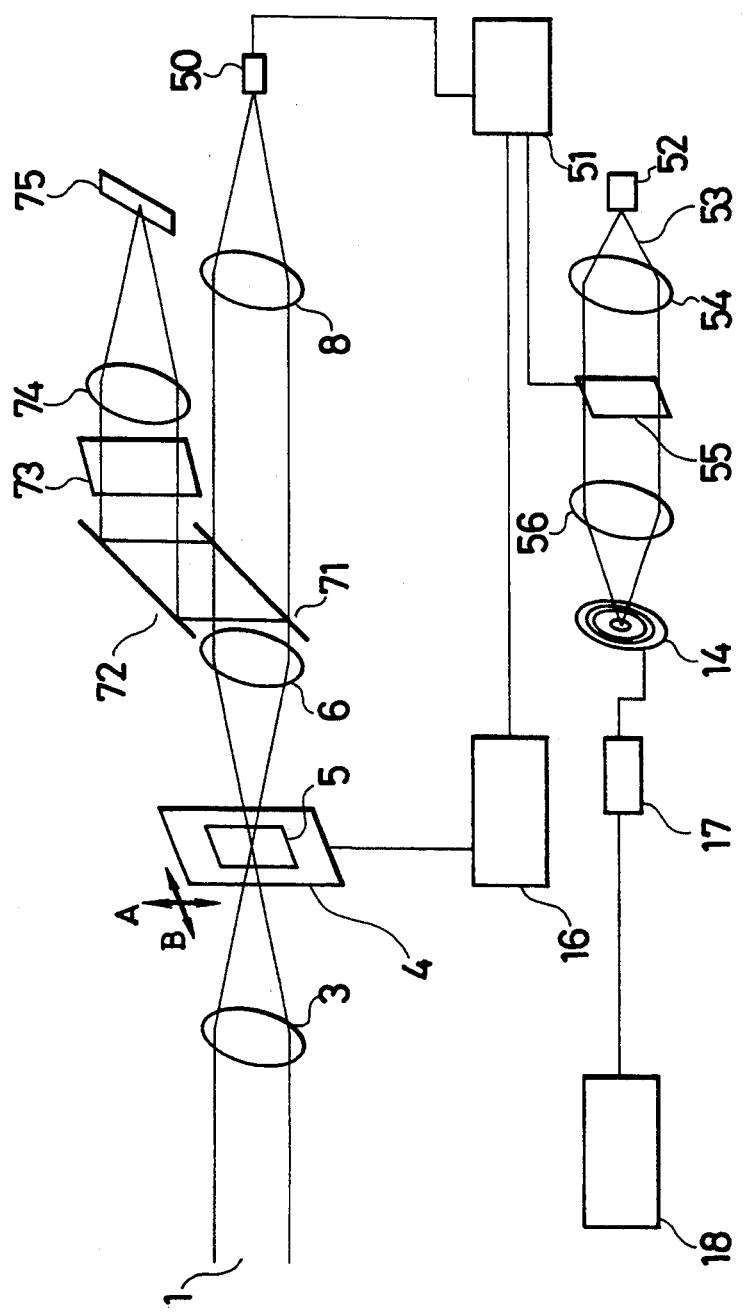
FIG. 6 shows schematically a third embodiment of an apparatus for identification of an object in accordance with the present invention.

FIG. 6 shows a third embodiment of the apparatus of the present invention. This figure is similar to the embodiment shown in FIG. 5, but includes a beam splitter 71, mirror 72, filter 73, lens 74 and linear sensor 75. The detecting circuit 51 comprises a device for operating a liquid crystal panel 55. The light beam emitting from the lens 6 is divided into two beams by a beam splitter 71. The beam transmitting through the splitter can form an image on the CCD 50, and the liquid crystal panel 55 displays the image, which is optically Fourier transformed. The beam reflected by the splitter 71 is reflected by a mirror 72, and passes through a wavelength filter 73, and forms the image on the linear sensor 75 by a lens 74. At this time, the sample 5 is moved in the direction A of FIG. 6. When the output at the specific position from the linear sensor 75 becomes lower, the nucleus of the leukocyte can be detected and centered at the specific position of the device for moving the sample. The image of the object can be positioned at the center of the image-forming system, on the basis of the detected position of the nucleus. Alternatively, the image of the leukocyte can be displayed at the center of the panel by the image processing technique.

In this case, as mentioned in Example 2, an AD converter of the input image signal, and a look-up table to convert in density the AD converted image digitalized data, and a density converting device, comprising a DA transducer for converting the density-converted data into analog signals are effectively provided between the CCD 50 and the detecting circuit 51. The composition and the other elements are similar to those of Example 2, and thus the description thereof is omitted.

Figure 7:
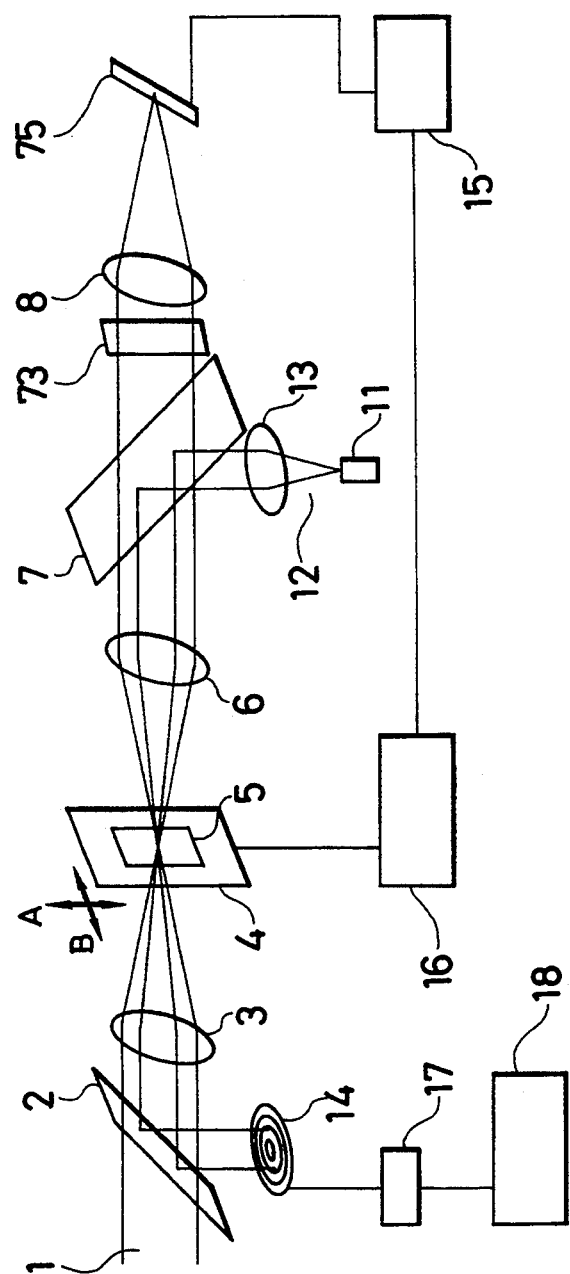
FIG. 7 shows schematically a fourth embodiment of an apparatus for identification of an object in accordance with the present invention.

The device for tracking the object can be combined as in Example 1. In this case, the configuration is shown in FIG. 7. The mask 9 and the photodetectors 10 become unnecessary and the linear sensor 75 is substituted for these elements. Further, the wavelength filter 73 is provided between the beam splitter 7 and the linear sensor 75. The detecting circuit 15 detects the output from the linear sensor 75. Therefore, the position of the nucleus of the leukocyte can be tracked. In this case, the processing of the signals from the ring detectors is similar to that of Example 1, and thus the description thereof is omitted.

EXAMPLE 4

Figure 8:
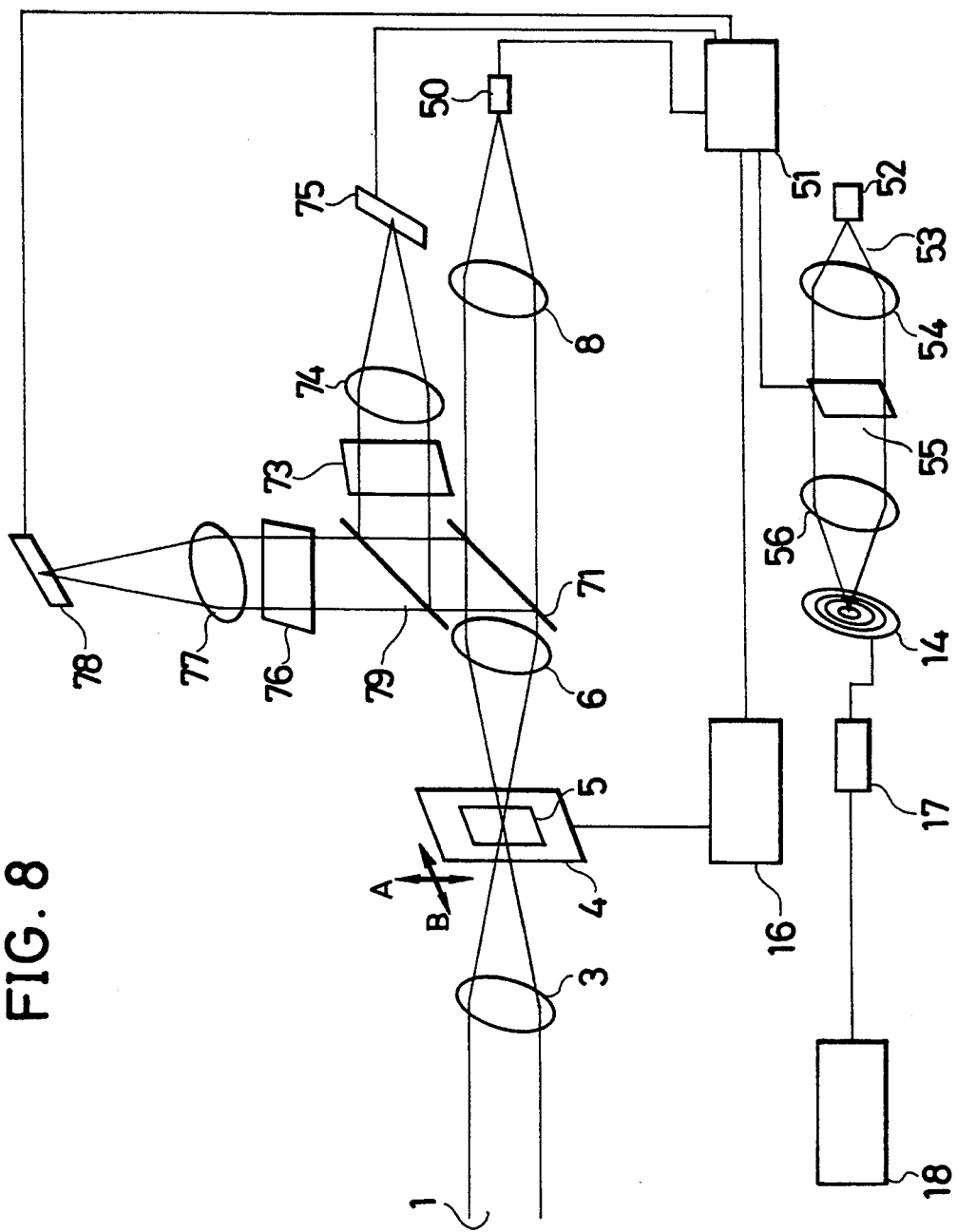
FIG. 8 shows schematically a fifth embodiment of an apparatus for identification of an object in accordance with the present invention.

In the device for tracking the position of the object, a plurality of linear sensors are provided to form different images with each different wavelength range. Each of the outputs so produced are processed to enable definite tracking of the position of the nucleus of the leukocyte to be identified. FIG. 8 shows one example of an optical apparatus having such feature. This is an apparatus in which a plurality of optical passages for a plurality of linear sensors are added to the composition of FIG. 6. The image of the sample is divided into two by a half-mirror 79, and each is formed respectively on a first linear sensor 75 and a second linear sensor 78. At this time, a wavelength filter 76 having higher transmissivity in the wavelength range of about 450 nm, and a lower transmissivity in a second wavelength range is provided. The nucleus of the leukocyte has a transmissivity entirely different from each of the two filters, while the other portions, such as erythrocytes, and the background have transmissivity similar to the two filters. Therefore, only the portion corresponding to the nucleus of the leukocyte can be accurately extracted or emphasized by subtracting the output of the linear sensor 75 from a multiple of the output of the linear sensor 76 with the appropriate coefficient. The detecting of the output of the line sensors and the calculation can be conducted by the detecting circuit 51. The tracking of the object or the leukocyte can be done as described in Example 3. Such addition of the plurality of optical passages for a plurality of linear sensors can be applied to the optical apparatus of Example 1.

EXAMPLE 5

Figure 9:
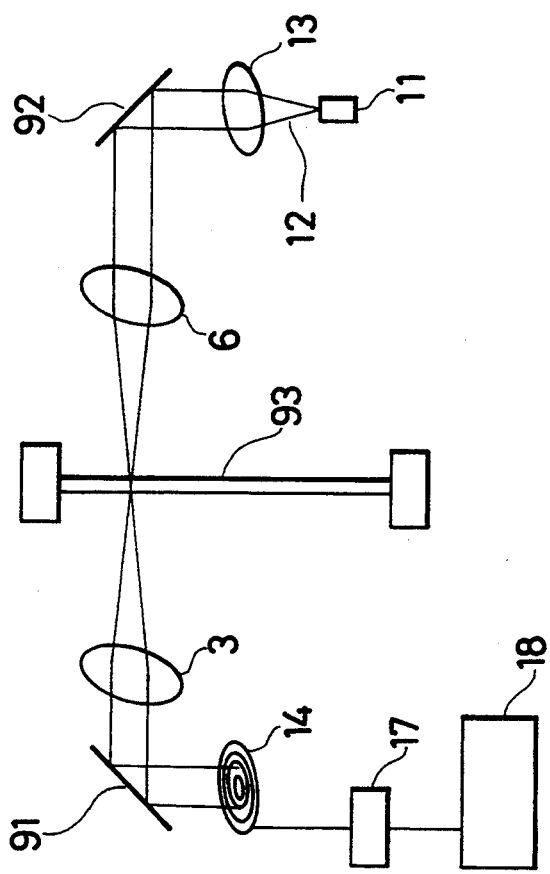
FIG. 9 shows schematically a sixth embodiment of an apparatus for identification of an object in accordance with the present invention.

In the above Examples, the device for tracking the position of an object comprises a combination of a moving device such as an X-Y stage, and an optical detecting device. The object may be flowing in a narrow tube through which a solution of the object flows, the diameter of which is slightly larger than the maximum diameter of the object to be identified among other flowing objects. The certain position of the tube is detected by the detector so as to track the object, or the position of the object. FIG. 9 shows the structure of the apparatus for such detection and tracking.

In FIG. 9, the optical system for Fourier transformation is the same as in Example 1. Therefore, the optical Fourier transformation is omitted. When the object is a leukocyte, blood should be diluted to be detected because it can flow easily in such a narrow tube, and further, each leukocyte and erythrocyte can be easily dissociated in the dilution. Particularly, the dissociation of an erythrocyte by a hemolyzing agent will reduce noise when the leukocyte is to be identified. The solution containing leukocytes as a solute flows through the tube 93, with the leukocytes flowing in a line. The tube is fixed at the position of focus of the lens 6, such that each of the leukocytes can cross or traverse sequentially to the coherent beam 12. When a leukocyte crosses the coherent beam 12, the amount of light detected by the ring detector will be significantly changed. The output of the ring detector 14 at the time of significant change is detected and used for identification of the object, or the leukocyte.

EXAMPLE 6

In this Example, the characteristic data is obtained by the ring detectors, as described in Examples 1 to 5. Only the identification processing in an identifying means 18 will be described in this Example.

The identification device 18 can give a logical identification of the object, by obtaining a distribution of the categories of the object to be identified. However, where the ranges in which all of the characteristic parameters may be present can possibly overlay each other, a neural network device of the layered type which represents each monolayer or multilayer perceptron is effective to correctly identify the object. Such a neural network device of the layered type can display the characteristic parameters of the object of each of the categories, and the desired outputs representing the categories with regard to a number of the objects. Therefore, binding weight values can be organized within the network, so as to give outputs representing the appropriate category to the object by the network. Consequently, even such categories which cannot be completely dissociated by a combination of digitalization logic can be identified. Therefore, the identification device 18 can comprise a known neural network device. In such a case, the construction of the neural network device may be hardware or software based. The type of learning algorithm does not need to be limited. For example, the structure of a multilayered perceptron having three or more layers can give the desired result only by error back propagation learning based on a well-known general delta theory.

EXAMPLE 7

In this Example, the characteristic data is obtained by the ring detectors, as described in Examples 1 to 5. Only the identification processing in an identifying device 18 will be described herein.

The identification device 18 can be operated, for example, by a fuzzy logic calculation device, without use of a neural network device. FIG. 3 shows such apparatus operated with fuzzy logic identification. For simplification of explanation the apparatus of FIG. 3 is operated with two categories and eight parameters, but only three parameters $x_1$, $x_2$ and $x_8$ are illustrated. For example, category 1 and category 2 to which the object is to be identified are shown in FIG. 3, and each of the averaged values with regard to each of the categories is respectively calculated experimentally from each of the parameters $x_1$ to $x_8$. If a convex monotonous decreasing function (membership function) is conceived with a convex point being the average of the parameters, the outputs of respective functions with regard to each of the categories can be calculated for the object to be identified. If each of the parameters with regard to the object is $x_1=a$, $x_2=b$ and $x_8=c$, the outputs of respective functions can be calculated as shown by dotted lines in FIG. 3. If the minimum of the function output with regard to category is the function output with regard to $x_2$, and the minimum of the function output with regard to category 2 is the function output with regard to $x_1$, it can be concluded that the object to be identified belongs to category 1, with the minimum being higher.

The number of the parameters, and the shape of the functions are just one example, which does not restrict the scope of the invention. The number of the parameters can be increased, and the shape of the functions can be of convex or concave in form. When the curve of the function is convex, the category having the highest minimum of the output should be selected. When the curve of the function is concave, the category having the lowest maximum of the output should be selected. FIG. 3 shows a simplified mountain (deltoid) in the curve of the function, but a figure such as a trapezoid, having a plateau around its peak, or a Gaussian distribution curve, can be present. The computer used for this processing can be a Von Neuman type, or an ordinary computing device.

EXAMPLE 8

Example 7 does not limit the slope to a monotonously non-decreasing function or monotonously non-increasing function. When such slope is set on the basis of its parameter dispersion, a significant result can be effected. The value evaluating this dispersion can be referred to as "variance ratio" and "standard deviation". For example, if such value is added to a denominator of a term determining the slope of the function, the higher dispersion of the parameters will give the gentler slope to the function. That is, when the parameters are widely dispersed, the value far from the average can be reevaluated.

EXAMPLE 9

Figure 4:
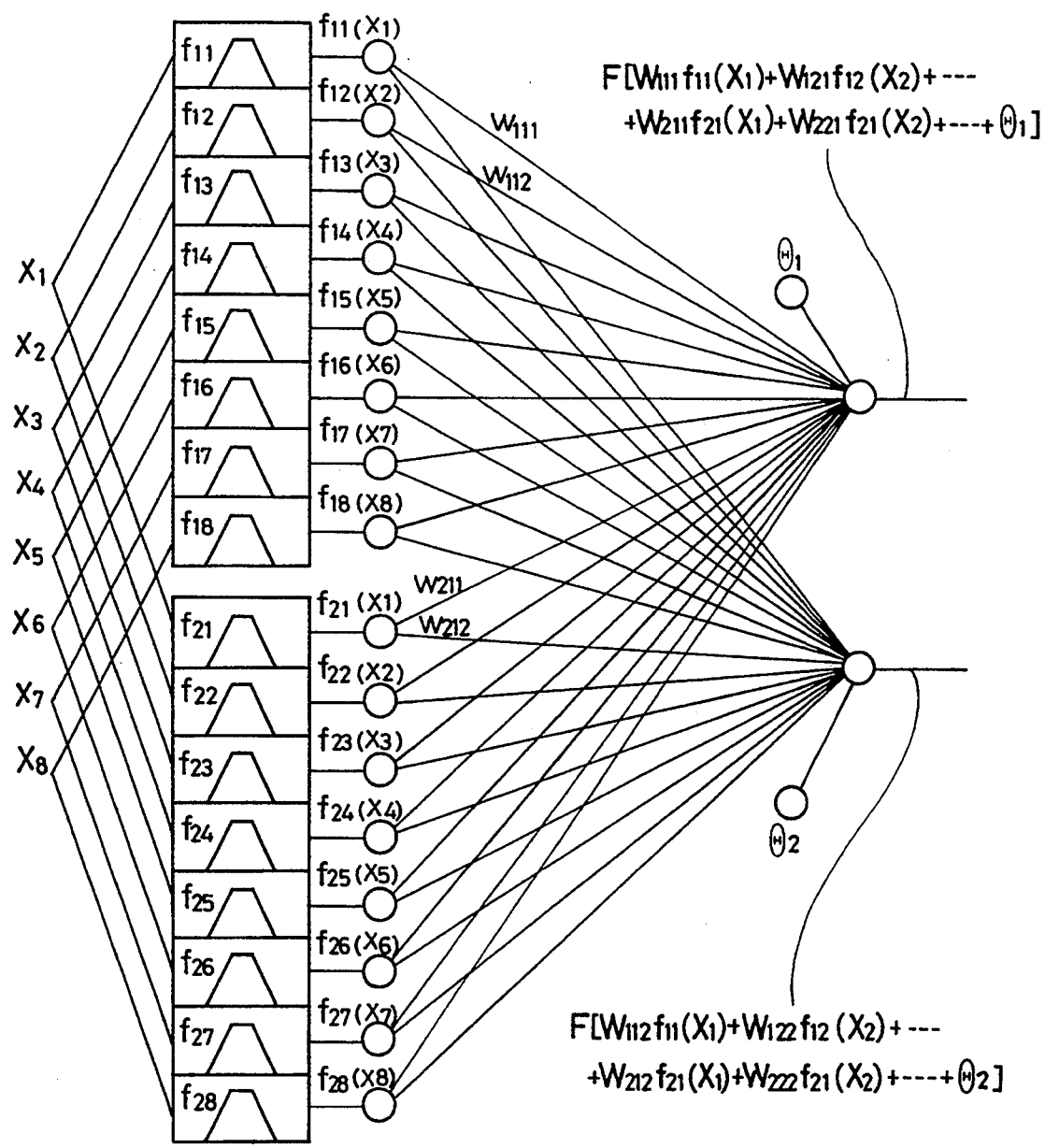
FIG. 4 is a schematic illustration showing the configuration of a means of identifying a component of the object to be identified in accordance with the present invention.

FIG. 4 schematically shows an optical apparatus for the identification of an object, by optically processing the pattern generated by the object.

In the apparatus described in Examples 7 and 8, the minimum of the output of each of the functions can give a correct identification. The outputs of respective functions in each of the categories with regard to each of the parameters are put into a neural network device such as a monolayered or multilayered perceptron device for identification of the object. Such a structure of the apparatus can give a new advantage for identification processing. FIG. 4 shows such structure of the apparatus for identification of an object in which each of the elements $x_1$ to $x_8$ for the characteristic vector X, which are outputs from the detecting circuit 17, are respectively multiplied by each of the functions corresponding to each of the categories and each of the parameters, so as to produce each of the outputs; the number thereof being the number of elements of vectors multiplied by the number of categories. Then, the apparatus learns on the basis of perception in which these outputs are put. In FIG. 4, $f_{ij}$ represents a function with regard to a category i corresponding to parameter $x_j$, and $W_{ijk}$ represents a weight for connecting a line from the output of the function with regard to the category i corresponding to parameter $x_j$ to output layer neuron indicating category k, in the neural network device of the monolayered perceptron type. $\Theta_i$ is a bias input indicating category i to put in an output layer neuron, and F is a monotonous non-decreasing function indicating input and output features of the output layer neuron. $\Theta_i$ may be a connecting weight factor, connecting from each of the bias neuron of output 1 to each of the output neurons. Among each of the parameters, a specific category can be emphasized, and in reverse, a specific category can be suppressed, thereby the significant result can be obtained even when the characteristic is visually vague. This learning algorithm need not be limited as in Example 2. When the device is of a monolayered perceptron, the learning algorithm based on a well-known delta rule, can produce a good result.

EXAMPLE 10

The identifying device can give a new effect by combining the construction of Examples 7 or 8 with Examples 6 or 9. In the configuration of Examples 7 or 8, the sum of the contributions from each of the parameters will determine the category identified, and then, in some cases, mistaken identification is possible when a large number of the parameters have a small contribution and a small number of the parameters have a great contribution. The categories which have been found to have a lower possibility from the apparatus of Examples 6 or 9 should be previously omitted so as to reduce the possibility for mistake.

Inversely, in the apparatus of Examples 7 or 8, while a large number of the parameters can give a correct response even when the input patterns are partly defective, a small number of the parameters can give a lower response, so that the correct identification cannot be attained. The combination of the result with the result obtained in the apparatus of Examples 6 or 9 will give correct identification.

In the components of Examples 7 or 8, even where the input pattern has a partially insufficient figure, most of the parameters can react correctly but a smaller number of the parameters would react with less response, so that correct identification cannot be afforded. Therefore, the result from the composition of Examples 6 or 9 should be combined with the result from that of Examples 7 or 8, so that correct identification can be produced.

The following significant results can be effected by the apparatus for identification of an object to be identified.

Firstly, characteristic parameters can be detected by a relatively inexpensive apparatus using inexpensive semiconductor lasers and liquid crystal panels, and the amount of data to be processed becomes significantly less, so that the object can be rapidly identified with a lower cost.

Secondly, because digitalization does not exert in contrast to digit image processing, a plurality of the parameters, which do not depend greatly on the configuration in a specific direction, can easily be obtained.

Thirdly, it is possible to select and amplify only the parameters which are significantly effective for identification, and then, a more stable processing for identification can be exerted.

We claim:

1. An optical apparatus for identifying an object or a species of the object, the object provided on a plane, comprising:
    a tracking means for tracking the position of the object to be identified, and;
    an identification means for identifying the object tracked by said tracking means, said identification means comprising:
        a first coherent light beam emitting source;
        a first lens assembly in line with said first coherent light beam emitting source for irradiating the object to be identified and the region surrounding thereto, to produce a resultant light beam projected through the object to be identified;
        a detection means for detecting said resultant light beam, said detection means provided with photodiodes included on a plurality of continuous arcs, the center of which is at the axis of said resultant light beam, in a plane on which Fraunhofer's diffraction patterns are formed with regard to the plane containing the object, each of said plurality of continuous arcs producing distinctive outputs; and
        a determination means in communication with said detection means for identifying the object using each of said outputs of said detection means, each of said outputs providing characteristic parameters of the object to be identified.

2. The optical apparatus in accordance with claim 1, wherein said first lens assembly includes an objective lens functioning to enlarge and track the object to be identified.

3. The optical apparatus in accordance with claim 1, wherein said continuous arcs are circles.

4. The optical apparatus in accordance with claim 1, wherein said continuous arcs are semicircles.

5. The optical apparatus in accordance with claim 1, wherein said tracking means includes a means for moving the object to be tracked in two dimensions.

6. The optical apparatus in accordance with claim 1, wherein said tracking means includes an elongated tube containing the object to be identified included in a solute, the width of said tube being as large as the maximum size of the object to be identified.

7. The optical apparatus in accordance with claim 1, wherein said identification means is operated by a neural network whose inputs include the outputs of said detection means.

8. The optical apparatus in accordance with claim 1, wherein said identification means is provided with a means for obtaining the average values of said characteristic parameters of a plurality of objects to be identified and a means for comparing particular characteristic parameter values with the average value of the particular characteristic parameter to produce a particular function for each object to be identified.

9. The optical apparatus in accordance with claim 8, wherein said identification means is provided with a means for determining the average slope of each of said functions based upon the extent of the variance of each of said characteristic parameters with regard to a plurality of objects to be identified.

10. An optical apparatus for identifying an object or a species of the object, the object provided on a plane, comprising:
    a tracking means for tracking the position of the object to be identified, and;
    an identification means for identifying the object tracked by said tracking means, said identification means comprising:
        a first lens assembly to alter the image of the object to be identified;
        an image sensor for picking up the image of the object to be identified from said first lens assembly;
        a coherent radiation beam source;
        a display for displaying the image obtained by said image sensor;
        a second lens assembly for directing a beam produced by said coherent radiation beam source to the image displayed on said display;
        a detection means for detecting the image displayed on said display, said detection means provided with photodiodes included on a plurality of continuous arcs, the center of which is at the axis of the displayed image, in a plane on which Fraunhofer's diffraction patterns are formed, each of said plurality of continuous arcs producing distinctive outputs, each of said outputs producing characteristic parameters of the object to be identified; and
        a determination means in communication with said detection means for identifying the object using the outputs provided by said detection means.

11. The optical apparatus in accordance with claim 10, wherein said identification means is provided, between said image sensor and said display with a means for modifying the density of the images of the objects to be identified in real-time, so as to improve the contrast of these images.

12. The optical apparatus in accordance with claim 10, wherein said tracking means includes a means for moving the object to be tracked in two dimensions.

13. The optical apparatus in accordance with claim 10, further including a third lens assembly, a filter and a linear sensor provided at the focal point of said third lens assembly for the object to be identified, said linear sensor comprising a plurality of linearly arranged photoelements in line with one of the directions in which the object is moved by said tracking means.

14. The optical apparatus in accordance with claim 10, wherein said identification means is operated by a neural network whose inputs include the output of said detection means.

15. The optical apparatus in accordance with claim 10, wherein said identification means is provided with a means for obtaining the average values of said characteristic parameters of a plurality of objects to be identified and a means for comparing particular characteristic parameter values with the average value of the particular characteristic parameter to produce a particular function for each object to be identified.

16. The optical apparatus in accordance with claim 15, wherein said identification means is provided with a means for determining the average slope of each of said functions based upon the extent of the variance of each of said characteristic parameters with regard to a plurality of objects to be identified.

* * * * *